United States Patent [19]

Moyer

[11] Patent Number: 4,920,121

[45] Date of Patent: Apr. 24, 1990

[54] ANXIOLYTIC ACTIVITY OF N-(2-METHOXYPHENYL)PIPERAZINE

[75] Inventor: John A. Moyer, New Hope, Pa.

[73] Assignee: American Home Products Corporation, New York, N.Y.

[21] Appl. No.: 411,066

[22] Filed: Sep. 22, 1989

[51] Int. Cl.[5] .......................................... A61K 31/495

[52] U.S. Cl. .................................................. 514/255

[58] Field of Search ...................................... 514/255

*Primary Examiner*—Stanley J. Friedman

*Attorney, Agent, or Firm*—Richard K. Jackson

[57] ABSTRACT

N-(2-Methoxyphenyl)piperazine as a useful anxiolytic agent.

3 Claims, No Drawings

ANXIOLYTIC ACTIVITY OF N-(2-METHOXYPHENYL)PIPERAZINE

BACKGROUND OF THE INVENTION

Anxiety is a psychiatric disorder that ranges in severity from very mild temporary disorders such as insomnia or stage fright to spontaneous panic attack with attending anticipation of doom or unreasonable terror. The benzodiazepine drugs are generally considered the drugs of choice for treatment of anxiety, although they are sometimes habituating and frequently cause ataxia and drowsiness. Buspirone is a new antianxiety drug which does not cause drowsiness, although it may cause headache or dizziness and sometimes nauses and diarrhea. Buspirone takes from one to two weeks to become effective, but it has advantages over the benzodiazepines in long term therapy by not causing functional impairment of the patient.

The ability of buspirone, a nonbenzodiazepine anxiolytic, to antagonize isolation-induced aggression in male mice at doses which do not produce debilitation [McMillen et al., Arch. Pharmacol. 335 454 (1987); McMillen et al., Drug Development Research 12 53 (1988)] is considered to be related to its recognition and action at the 5-$HT_{1A}$ receptor. The anxiolytic profile of additional nonbenzodiazepine compounds can be established by comparison of their activity profiles with that of buspirone in standard experimental test procedures.

N-(2-Methoxyphenyl)piperazine is a known compound. In the rat, it has been reported to be a metabolite of the antipsychotic agent millipertine [Caccia et al., Biochem. Pharmacol. 34 (3) 393 (1985)]. It has been shown to possess antihypertensive properties [Morphis et al., Proc. Soc. Exp. Biol. Med., 101 174 (1959)] and to block dopaminergic effects in the brain [Minard et al., J. Pharm. Pharmacol. 31 (2) 91 (1979)] and to block conditional avoidance responding (CAR) in the rat [Martin et al., Eur. J. Pharmacol. 156 223 (1988)], which is characteristic of antipsychotic agents.

DESCRIPTION OF THE INVENTION

In accordance with this invention, there is provided a method for the symptomatic relief of anxiety disorders which comprises administering, orally or parenterally, to a patient suffering from anxiety, an antianxiety amount of N-(2-methoxyphenyl)piperazine or a pharmaceutically acceptable salt thereof. The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The anxiolytic propeties of N-(2-methoxyphenyl)piperazine were shown to parallel the known anxiolytic properties of buspirone by establishing its activity in antagonizing isolation-induced aggression, evaluating its activity in the serotonin syndrome procedure as an in vivo assessment of activity at the post synaptic 5-$HT_{1A}$ receptor, and by assessing its activity in the discrete trial conditioned avoidance test.

The isolation-induced aggression test was conducted with male mice in an adaptation of the method of DaVanzo et al., Psychopharmacology, (Berlin) 9 210 (1966) whereby male Charles River, CF-1 mice, 16–20 g in weight were individually housed for a period of three weeks and then trained to attack an intruder mouse which had been group housed (10/cage). Either N-(2-methoxyphenyl)piperazine or 0.25% Tween 80® was administered intraperitoneally to the aggressive mice 60 minutes before testing. The total fighting time (TFT) in seconds was recorded during a 3 minute test period upon introduction of the intruder mouse into the cage of the aggressive mouse.

As an antagonist of isolation-induced aggression in male mice, N-(2-methoxyphenyl)piperazine reduced total fighting time at 0.5, 1.0 and 3.0 mg/kg i.p. to levels of 5.1, 0.7 and 0.1 seconds respectively, in relation to 15.7 seconds total fighting time for vehicle controls.

In order to differentiate between specific antiagressive effects and an inhibition of fighting due to debilitation, rotorod motor coordination (RMC) tests were conducted according to an adaptation of the method of Dunham et al., J. Am. Pharm. Assc. 46 (3), 208 (1957) and Malick et al., Drug Development Research, 4 61 (1983) whereby male, Charles River mice, CF-1 were administered N-(2-methoxyphenyl)piperazine or vehicle (0.25% Tween 80®) intraperitoneally 60 minutes before placing them on a rotorod treadmill for mice (Ugo Basile, Varese, Italy). The amount of time spent on the rod (maximum of 60 seconds) was recorded and compared with the vehicle treated control animals. In this study, it was found that the N-(2-methoxyphenyl)-piperazine treated mice did not become debilitated by the compound until a dosage of 30.0 mg/kg or more was administered which is at least ten times the dose that antagonized aggressive activity in the previous study. In comparison, the minimum effective dose (mg/kg i.p.) of buspirone in the isolation induced aggression study was 10.0 mg/kg and greater than 60.0 mg/kg in producing ataxia as evaluated by the rotorod motor coordination study.

N-(2-methoxyphenyl)piperazine has been previously shown to have potent affinity for 5-$HT_{1A}$ receptors [Ki=9.5 nM: Martin et al., European J. of Pharmacol. 156 223 (1988)]. In vivo postsynaptic 5-$HT_{1A}$ activity was confirmed in tests showing N-(2-methoxyphenyl)-piperazine has weak partial agonist activity in serotonin syndrome tests. Serotonin syndrome tests were conducted according to the method of Smith et al., Pharmacol. Biochem. and Behav., 24 1513 (1986).

Male Sprague-Dawley CD rats (Charles River) weighing 200–300 g were housed 6/cage with food and water available ad libitum. Animals were allowed to acclimate to the animal colony for at least 1 week prior to testing. Rats were placed individually into plexiglas® observation cages with a layer of bedding covering the bottom. In dose response studies, N-(2-methoxyphenyl)piperazine (1, 3.3, 10 and 33 mg/kg, i.p.) and vehicle (0.25% Tween 80®) were administered 15 minutes prior to administration of 5.6 mg/kg i.p. 8-hydroxy-N,N-dipropyl-amino-tetralin (8-OH-DPAT), a specific 5-$HT_{1A}$ agonist. During the 15 minute pretreatment, subjects were scored for the presence of the 5-HT syndrome (agonist activity). After the 8-OH-DPAT injection, all subjects were scored for an additional 15 minutes to identify antagonist activity. Scoring the 5-HT syndrome consisted of rating the following behaviors: (1) forepaw treading, (2) head-weaving, (3) tremor, (4) hindlimb abduction, (5) flattened body posture, and (6) Straub tail on a 4-point ranked intensity scale with a maximum score of 18. Results were expressed as mean total score (+/−SEM) for induction of syndrome and for antagonism of syndrome. In this test, N-(2-methoxyphenol)piperazine displayed agonist activity at 10 and 30 mg/kg i.p., while at 33 mg/kg i.p. it antagonized the serotonin syndrome induced by 8-OH-DPAT. Buspirone also produced a partial agonist profile in this procedure (agonist $ED_{50}=7$ mg/kg i.p., antagonist $ED_{50}=4$ mg/kg i.p.

The conditioned avoidance responding (CAR) test was conducted in male CD rats (Charles River) maintained at approximately 400–450 g body weight. Rats trained previously were placed in Plexiglas® experimental chambers equipped with a response lever, house light and sonalert. The steel grid chamber floor is wired for presentation of an electric shock. Each trial consists of a fifteen second warning tone conditioned stimulus, continuing for an additional fifteen seconds accompanied by electric shock (unconditioned stimulus). The rat can terminate a trial at any point by depressing the response lever. A response during the initial fifteen second warning tone ends the trial before shock delivery and is considered an avoidance response. A response occurring during shock delivery is an escape response. The test compound, N-(2-methoxyphenyl)-piperazine was administered intraperitoneally to the rats thirty minutes before the test was run. The $ED_{50}$ of the test compound is calculated from the percentage reduction in avoidance responding and represents that dose at which only half the responses are made. Martin et al., European J. of Pharmacol. 156 223 (1988) reported an $ED_{50}$ of 5.6 mg/kg i.p. In accordance with the instant test procedure, an $ED_{50}$ of 10.6 mg/kg i.p. was established.

Thus, N-(2-methoxyphenyl)piperazine and the non-benzodiazepine anxiolytic buspirone share activity in the antagonism of isolation-induced aggression procedure and in the conditioned avoidance responding procedure, as well as activity at the $5\text{-HT}_{1A}$ receptor. As such, N-(2-methoxyphenyl)piperazine is considered to be an anxiolytic agent useful in treating anxiety disorders. As such, it may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g., as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific anxiety disorder must be subjectively determined by the attending physician. The variables involved include the specific state of anxiety and the size, age and response pattern of the patient. Based upon the activity profile and potency of N-(2-methoxyphenyl)piperazine relative to the analogous properties of buspirone, an initial human dose within the range of about 20 to about 30 mg/day, by single or divided, oral administration, should be appropriate. The containing dose may then be modified to achieve the desired effect, within the range of about 10 to about 100 mg/day, as personalized for the patient.

What is claimed is:

1. A method for symptomatic relief of anxiety disorders which comprises administering, orally or parenterally, to a patient suffering from anxiety, an antianxiety amount of N-(2-methoxyphenyl)piperazine or a pharmaceutically acceptable salt thereof.

2. A method of claim 1 in which N-(2-methoxyphenyl)piperazine is administered orally to said patient in an amount of from about 10 to about 100 milligrams per day.

3. A method of claim 1 in which N-(2-methoxyphenyl)piperazine is administered orally to said patient in an amount of from about 20 to about 30 milligrams per day.

* * * * *